United States Patent [19]

Dow et al.

[11] Patent Number: 5,061,700

[45] Date of Patent: Oct. 29, 1991

[54] GLYCERYL ACETATE OINTMENT VEHICLES

[75] Inventors: Gordon J. Dow, 506 Sequoia Ave., San Anselmo, Calif. 94960; Debra A. Dow, San Rafael, Calif.

[73] Assignee: Gordon Jay Dow, Mill Valley, Calif.

[21] Appl. No.: 438,372

[22] Filed: Nov. 16, 1989

[51] Int. Cl.$^5$ .................. A61K 9/06; A61K 31/56; A61K 31/57; A61K 31/58

[52] U.S. Cl. .................. 514/169; 514/171; 514/172; 514/174; 514/176; 514/177; 514/178; 514/179; 514/180; 514/181; 514/182; 514/969

[58] Field of Search .................. 514/969, 169-182

[56] References Cited

U.S. PATENT DOCUMENTS

| | | | |
|---|---|---|---|
| 3,892,856 | 7/1975 | Hill et al. | 424/241 |
| 3,934,013 | 1/1976 | Poulsen | 424/239 |
| 3,978,203 | 8/1976 | Wise | 424/22 |
| 3,980,778 | 9/1976 | Ayer et al. | 424/243 |
| 3,981,910 | 9/1976 | Offermanns et al. | 260/516 |
| 4,017,615 | 4/1977 | Shastri et al. | 424/241 |
| 4,055,653 | 10/1977 | Offermanns et al. | 424/275 |
| 4,069,322 | 1/1978 | Bodor et al. | 424/241 |
| 4,070,462 | 1/1978 | Ecker | 424/243 |
| 4,083,974 | 4/1978 | Turi | 424/241 |
| 4,218,447 | 8/1989 | Isaac et al. | 424/241 |
| 4,543,360 | 9/1985 | von Angerer et al. | 514/415 |
| 4,661,511 | 4/1987 | von Angerer et al. | 514/415 |
| 4,847,297 | 7/1989 | Chandra | 514/562 |
| 4,871,723 | 10/1989 | Makino et al. | 514/167 |

OTHER PUBLICATIONS

Makino et al., C.A. 112:240544e (1990) of U.S. Pat. No. 4,871,723, Oct. 3, 1989.
Makino et al., C.A. 110:121409p (1989) of JP 63 99014, Oct. 15, 1986.
Ono et al., C.A. 110:199242y (1989) of JP 63 255 227, Oct. 21, 1988.
Ono et al., C.A. 110:1992432 (1988) of JP 63 255228, Oct. 21, 1988.
Ono et al., C.A. 109:116054u (1988) of JP 62 238216, Oct. 19, 1987.
Wise, C.A. 85:130548a (1976) of U.S. Pat. No. 3,918,203, Aug. 31, 1976.

*Primary Examiner*—Shep K. Rose
*Attorney, Agent, or Firm*—Townsend and Townsend

[57] ABSTRACT

Compositions of matter serving as topical ointment vehicles and comprising a glyceryl acetate, preferably triacetin, and an oleaginous material that can be combined with a medicament, preferably a corticosteriod, are described. The glyceryl acetate component functions as a solvent for the medicament. Additionally, methods of use for treating skin disorders comprising the topical application of a therapeutically effective amount of a medicament in a composition of the invention are detailed.

17 Claims, No Drawings

GLYCERYL ACETATE OINTMENT VEHICLES

BACKGROUND OF THE INVENTION

1. Field of the Invention

This invention relates to compositions of matter serving as topical ointment vehicles (bases) and comprising a glyceryl acetate, and an oleaginous material that can be combined with a medicament (drug substance). More particularly, it relates to ointment vehicles containing corticosteroids and methods for their use in treating skin disorders.

2. Brief Description of the Relevant Art

Ointments are one of the oldest types of vehicles for the incorporation of medicaments applied topically to treat disorders of the skin. The ointment vehicle provides a means of distributing the medication uniformly over the affected skin surface and maintaining it there for sufficient time in which the therapeutic effect can occur. Early ointment vehicles were comprised primarily of fats, greases, and petrolatum, i.e., oleaginous materials. These materials are not water washable, which detracts from cosmetic properties. They are occlusive, however, which causes skin hydration from the sweat accumulating at the skin-ointment interface and such hydration favors medicament penetration into the skin.

Most medications, especially corticosteroids, have very slight solubility in petrolatum and, therefore, must be incorporated into petrolatum as well dispersed, finely divided particles. The efficacy of medicaments in petrolatum ointment vehicles is often less than that expected from the medicament incorporated therein.

An ideal composition for a topical ointment vehicle would allow complete release of a medicament, such as a corticosteroid, from the ointment and also would achieve good penetration into the skin through occlusion or other mechanisms. Additionally, some degree of water washability would enhance the cosmetic value of the vehicle. An optimum manner of obtaining good penetration into the skin is to dissolve the medicament in the ointment vehicle or a component thereof. The medicament must not be excessively soluble in the vehicle, however, or its release from the ointment may be impeded.

The present invention seeks to remove some of the difficulties encountered with known ointment vehicles. This invention discloses the incorporation of a glyceryl acetate, preferably triacetin, into various oleaginous ointment vehicles. The use of a glyceryl acetate to dissolve the medicament alleviates the need to grind the drug substance into fine particles and to disperse the insoluble particles into the ointment vehicle, thus resulting in enhanced efficacy of the medicament. Also, vehicles of the present invention have somewhat improved water washability, when compared with petrolatum vehicles, without sacrifice of the necessary occlusive properties.

Discussion of ointment vehicles containing steroids is found in the following publications, all of which are incorporated herein by reference. U.S. Pat. No. 3,892,856 describes a steroid ointment formulation wherein the solvent for the corticosteroid is polyethylene glycol. U.S. Pat. No. 4,017,615 describes an ointment vehicle for medicaments, including anti-inflammatory steroids, containing propylene carbonate. U.S. Pat. No. 4,070,462 refers to an ointment containing esters of the steroid, betamethasone, in which a glycol solvent is used. U.S. Pat. No. 4,083,974 describes ointment and liquid preparations for anti-inflammatory steroids containing polyoxypropylene 15 stearyl ether as a solubilizing agent. U.S. Pat. No. 3,934,013 refers to pharmaceutical ointments wherein the solvents for anti-inflammatory steroids selected from the group consisting of water, glycerin, propylene carbonate, glycols, polyethylene glycol, dipropylene glycol, and mixtures thereof. U.S. Pat. No. 3,980,778 describes diflurasone diacetate ointments containing a solvent selected from the group consisting of propylene glycol, butane-2,3-diol, and 1,3-butanediol.

Triacetin (1,2,3 propanetriol triacetate; glyceryl triacetate), is listed as a pharmaceutical plasticizer, but not as a pharmaceutical solvent, in the U.S. Pharmacopeia/National Formulary 1075-76, 1492 (1985). It is also used as an antifungal drug and as a fixative in perfumery, in addition to certain industrial applications, see *The Merck Index* (10th ed.) p. 9407 (1983).

Triacetin and monoacetin, have been listed as one of many general pharmaceutical carriers/diluents for primarily systemic administration of specific compounds, see U.S. Pat. No. 4,543,360, and its divisional, U.S. Pat. No. 4,661,511 (for 2-(hydroxyphenyl)-indole or 2-($C_2$-$C_6$-alkanoxyloxyphenyl)indole compounds); U.S. Pat. No. 4,218,447 (for acyl derivatives of hellebrigenin); U.S. Pat. No. 3,981,910, and its continuation-in-part, U.S. Pat. No. 4,055,653, (for sulfur-containing trialkoxybenzoylamino carboxylic acids); and U.S. Pat. No. 4,847,297 (for penicillamine). (These publications are incorporated herein by reference.)

U.S. Pat. No. 4,069,322 describes oral and topical delivery of pro-drug forms of anti-inflammatory steroids. Topical carriers listed therein include a liquid solution comprised of a pro-drug and pure triacetin.

SUMMARY OF THE INVENTION

This invention relates to compositions of matter serving as topical ointment vehicles and comprising a glyceryl acetate, preferably triacetin, and an oleaginous material that can be combined with a medicament, preferably a corticosteroid. The glyceryl acetate component functions as a solvent for the medicament. Additionally, the present invention provides methods of use for treating skin disorders comprising the topical application of a therapeutically effective amount of a medicament in a composition of the invention.

DETAILED DESCRIPTION OF THE INVENTION AND PREFERRED EMBODIMENTS

The ointment vehicles of the present invention are comprised of an oleaginous material and a glyceryl acetate to which a medicament can be added. Many surfactants, thickeners, auxiliary solvents, and additives (the latter comprising buffers, penetrants, stabilizers, and preservatives) also may be incorporated.

In sum, the compositions of this invention, to which a medicament may be added, have the following components and approximate operable and preferred concentrations (concentrations are given in percent by weight):

| Ingredient | Operable Conc. | Preferred Conc. |
| --- | --- | --- |
| Glyceryl Acetate | 0.25–30 | 0.5–12 |
| Oleaginous Material | 30–99.75 | 45–99.5 |
| Surfactant | 0–20 | 1–5 |
| Thickener | 0–50 | 2.5–35 |
| Auxiliary Solvent | 0–29.75 | 0–11.5 |

| Ingredient | Operable Conc. | Preferred Conc. |
| --- | --- | --- |
| Additives | 0–5 | 0–3 |

Each ingredient category is listed in the singular; however, it is understood that two or more ingredients from each category may be used to make the ointment vehicle in this invention. The chemicals from each category of ingredients should be pharmaceutically acceptable compounds and should be sufficiently pure to be used on the skin safely.

One or more glyceryl acetates are essential to the present invention to serve as a solvent for the medicament. The glyceryl acetates are of the general formula $C_3H_5(CH_3COO)_n(OH)_{3-n}$, wherein n is 1, 2, or 3. These include monoacetin (1,2,3 propanetriol monoacetate) wherein n=1: diacetin (1,2,3 propanetriol diacetate) wherein n=2; triacetin (1,2,3 propanetriol triacetate;) wherein n=3; and mixtures thereof. The glyceryl acetate vehicles of the present invention are versatile, emollient, stable, and nonirritating.

The preferred glyceryl acetate is triacetin. A benefit of this glyceryl acetate vehicle, when the concentration of triacetin is 10% or greater, is the antifungal action, providing a combination of therapeutic antifungal and, when the medicament is a corticosteroid, anti-inflammatory effects.

The optimum amount of glyceryl acetate material depends upon the medicament(s) being incorporated in the ointment vehicle, its concentration(s), and its solubility characteristics. Generally, an amount of glyceryl acetate just sufficient to solubilize the drug substance at 20° C. is preferred. Once the amount of the medicament and the corresponding amount of the glyceryl acetate has been established, then the amount of surfactant(s), thickener(s), auxiliary solvent(s), and/or additive(s), if any is selected. The oleaginous material makes up the balance of the composition to obtain a concentration of 100 percent by weight.

The oleaginous material used in this invention can be any oily or greasy material and, preferably, is selected from the group consisting of paraffins or a combination of paraffins ranging from liquids (e.g., mineral oil) to semisolids (e.g., petrolatum and white petrolatum) to solids (e.g., paraffin wax); silicones (known as polysiloxanes), preferably the moieties attached to the polysiloxane are hydrocarbon moieties having from 1-8 carbons, such as lower alkyl, lower alkenyl, phenyl, alkyl-substituted phenyl, and phenyl alkyl, such as benzyl, with hydrocarbon moities having alkyl groups containing 1 to 3 carbons, such as dimethicone (dimethylpolysiloxane), being most preferred; lanolins, including anhydrous lanolin and essentially anhydrous derivatives thereof; and mixtures thereof.

Although not required in all cases, one or more surfactants may be contained in a vehicle of this invention to provide a stable and uniform dispersion of the glyceryl acetate in the oleaginous material. Suitable surfactants include those that are acceptable for topical application and are selected from the following types: nonionic, amphoteric, anionic, and cationic. Such suitable surfactants are well known to those skilled in the art. Representative examples of those surfactants that can be used in this invention are described in Martin & Cook, *Remington's Practice of Pharmacy* (12th ed.), pp. 219–26 (1961); Harry, R. G., *Cosmetics: Their Principles and Practice*, pp. 396–98 and 413–17 (1965); Sargarin, E., *Cosmetic Science & Technology*, pp. 328–33, 1060–63 and 1254 (1967) (these references are incorporated herein by reference). Preferred surfactants are of the nonionic type and have a hydrophilic-lipophilic balance (HLB) value of less than 7 or are combinations of nonionic surfactants with an overall HLB of less than 7. Examples of preferred surfactants are propylene glycol stearates, sucrose distearate, cholesterol, soya sterols, lanolin-derived sterols (such as lanolin alcohol), glyceryl stearates, sorbitan stearates, sorbitan monooleate, sorbitan sesquioleate, steareth 2, sorbitan palmitate, sorbitan trioleate, and mixtures thereof.

Various pharmaceutical thickeners known to those skilled in the art may be used in the present invention, although a thickener is not required. Preferred thickeners are selected from the group consisting of colloidal alumina, colloidal silicon, polyethylene, natural waxes (including spermaceti and white beeswax), fatty acids (such as stearic acid), fatty alcohols (such as stearyl alcohol), fatty amides having from 10–22 carbon atoms, synthetic waxes, microcrystalline waxes, paraffin waxes, and hydrophilic thickening agents, with polyethylene, white beeswax, and microcrystalline wax being most preferred. Examples of hydrophilic thickening agents include carbomers (such as carbomer 934); cellulose derivatives (such as hydroxypropylcellulose); and natural gums (such as tragacanth). When hydrophilic thickeners are employed, such thickeners are incorporated in the glyceryl acetate phase during processing.

Auxiliary solvents, although not necessary, may be used in this invention to increase the solubility of the medicament in the ointment or to reduce the amount of glyceryl acetate needed. The total amount of glyceryl acetate and auxiliary solvent should not exceed a concentration of about 30 percent by weight, preferably about 12 percent by weight. Such auxiliary solvents must be pharmaceutically acceptable and must be miscible with the glyceryl acetate component. Preferred agents are glycols such as propylene glycol (1,2 propylenediol), 2,3 butylene glycol (2,3 butanediol), and hexylene glycol (2-methyl-2,4-pentanediol); propylene carbonate; glycerin; polyethylene glycols and polypropylene glycols, said polyethylene and polypropylene glycols having molecular weights from 100 to 20,000 (e.g., polyethylene glycol (PEG) 300); benzyl alcohol; and mixtures thereof.

Numerous additives known to those skilled in the art, although not necessary, may be included in the compositions of the present invention. These include, but are not limited to, the following types: buffers, penetrants, stabilizers, preservatives, colors and fragrances.

Examples of suitable buffers (and acidifying agents) include organic acids (such as citric acid), salts of organic acids (such as sodium citrate), inorganic acids (such as phosphoric acid), inorganic bases (such as sodium hydroxide), inorganic salts (such as sodium biphosphate), and mixtures thereof.

Suitable penetrants include, but are not limited to, dimethylformamide, dimethylacetamide, tetrahydrofuran, tetrahydrofurfuryl alcohol, and 1-dodecylazacycloheptan-2-one, and dialkyl sulfoxides having from 2 to 22 carbons per alkyl group, such as dimethylsulfoxide.

Stabilizers are generally used to enhance the chemical stability of the medicament and may include antioxidants (such as ascorbic acid, alpha-tocopherol, butylated hydroxyanisole (BHA), butylated hydroxytoluene (BHT), propyl gallate, and ascorbyl palmitate); chelating agents (such as ethylenediamine tetraacetic acid and its salts); and ultraviolet (UV) absorbers (such as benzophenone-3).

Preservatives, also known as antimicrobial preservatives, that are suitable for use in this invention are well known to those skilled in the art. Examples of such preservatives include, but are not limited to, the group consisting of imidurea, benzyl alcohol, methylparaben, propylparaben, butylparaben, sorbic acid, potassium sorbate, dehydroacetic acid, sodium dehydroacetate, chloroxylenol, and quaternium-15.

The ointment vehicle of the present invention may be made from the above-specified ingredients by thoroughly mixing them together. Solids materials may be dissolved in liquid materials, dispersed using high shear, or melted to facilitate incorporation into the ointment vehicle.

The manufacturing process generally involves the preparation of two phases (oleaginous phase and glyceryl acetate phase), which are combined in the final stages of manufacturing with vigorous mixing. Mixing is accomplished with the phases int eh liquid or semisolid state. It is preferred that the phases be mixed in the liquid state, typically at elevated temperatures in the early stages of mixing. Mixing should continue as the temperature is reduced and until a semisolid consistency develops. The exposure of the glyceryl acetate to excessive heat for extended periods of time should be avoided. The components of the oleaginous phase include the oleaginous material and the surfactant. Thickeners and additives may be included in the oleaginous phase if they are lipophilic in nature. The glyceryl acetate phase consists of the glyceryl acetate, the medicament, any auxiliary solvent, any hydrophilic additives, and any hydrophilic thickeners. Various alternate methods of making this ointment vehicle will be known to those skilled in the art. The processing equipment that may be used to manufacture the vehicle can include heated or steam jacketed kettles, propeller mixers, homogenizing mixers, heat exchanger, colloid mills, roller mills, and kettles with side-scraping mixers.

A wide variety of medicaments are suitable for inclusion in the glyceryl acetate ointment vehicle of this invention for the topical treatment of various skin diseases and disorders. These medicaments should be in a concentration range of approximately 0.01-10 percent by weight. Corticosteroids with anti-inflammatory activity are particularly well suited, and their concentration range should be approximately 0.01-2.5 percent by weight. These corticosteroid medicaments include, but are not limited to, the following: hydrocortisone, hydrocortisone acetate, hydrocortisone valerate, hydrocortisone butyrate, desonide, triamcinolone acetonide, betamethasone valerate, betamethasone dipropionate, betamethasone benzoate, clobetasol propionate, halcinonide, desoximethasone, amcinonide, fluocinonide, fluandrenolide, alclometasone dipropionate, fluocinolone acetonide, diflorasone diacetate, and mometasone furoate.

Other steroid medicaments may be delivered to the skin for local therapeutic effect in the ointment vehicle of this invention. These steroid medicaments include sex hormones (such as estradiol) and other steroid compounds (such as spironolactone).

Drug substances used for the treatment of disturbances in hair growth, including baldness or excessive hairiness, may be effectively formulated in the present vehicle. Two examples of such drug substances are minoxidil and antiandrogenic compounds.

Antimicrobial drug substances may be effectively incorporated as well. Such medicaments includes the following classes of drugs: antibiotics, including tetracycline, clindamycin, erythromycin, bacitracin, neomycin, polymyxin, and chloramphenicol; antifungal drug substances, including miconazole, tolnaftate, clotrimazole, and ketoconazole; and antiseptics, including silver sulfadiazine, chlorhexidine, and povidone iodine.

Other medicaments that may be successfully incorporated include antihistamines (such as diphenhydramine), local anesthetics (such as didocaine and benzocaine), keratolytics (such as sulfur and salicylic acid), antipsoriatic drugs (such as anthralin), antiviral drugs (including acyclovir, fluorouracil, etc.), and other topically active drugs (including retinoids, such as tretinoin, and coal tar and its extract). These are representative examples only and should not be construed to limit the scope of this invention.

The present invention also includes methods of treating skin disorders comprising applying to the skin a therapeutically effective amount of a medicament incorporated in a vehicle comprising a glyceryl acetate and an oleaginous material. By therapeutically effective amount, it is meant a concentration amount in the range of approximately 0.01-2.5 percent by weight for corticosteroids and approximately 0.01-10 percent by weight for other medicaments. The therapeutically effective amount will vary depending upon the medicament chosen, the type and severity of the disease or disorder, the age of the patient, the recommendation of the attending physician, and other relevant factors. The ointment vehicle is applied to the affected area in an amount sufficient to cover the area and in a frequency from about every other day to about six times a day, preferably one to four times a day. When an antiinflammatory agent is present, the following conditions can be treated: psoriasis, contact dermatitis, atopic dermatitis, neurodermatitis, lichen planus, eczema, intertrigo, dyshidrosis, seborrheic dermatitis, exfoliative dermatitis, solar dermatitis, stasis dermatitis, anogenital and senile pruritus, and other steroid-responsive dermatoses.

EXAMPLES

The following examples serve to illustrate, but not limit, the compositions and methods of the present invention. It will be apparent to those skilled in the art that many modifications may be practiced without departing from the purpose and intent of this disclosure.

EXAMPLE 1

An ointment base having the following composition:

| Ingredients | Concentration (Percent by Weight) |
| --- | --- |
| Triacetin | 5.0 |
| Microcrystalline Wax | 35.0 |
| Mineral Oil | 60.0 |

Procedure: to make the oleaginous phase, the mineral oil and microcrystalline wax are melted together by heating to 75°-85° C. and mixed. With the oleaginous phase of about 55° C., the triacetin is added to the oleaginous phase while mixing. Mixing should be of sufficient intensity to disperse the triacetin finely and uniformly. Mixing is continued while cooling the ointment to 30° C. or lower.

EXAMPLES 2-3

Ointment bases having the following composition:

| Ingredients | Examples: | |
|---|---|---|
| | 2 | 3 |
| | Concentration (Percent by Weight) | |
| Triacetin | 5.0 | 10.0 |
| Sorbitan Monooleate | 2.5 | 0.0 |
| Sorbitan Sesquioleate | 0.0 | 5.0 |
| White Petrolatum | 92.5 | 85.0 |

Procedure: the petrolatum and sorbitan monooleate or sorbitan sesquioleate (oleaginous phase) are warmed to 35°-40° C. and mixed. While mixing, the triacetin is added to the oleaginous phase. Mixing should be of sufficient intensity to disperse the triacetin finely and uniformly. Mixing is continued while cooling the product to room temperature.

EXAMPLE 4

An ointment base having the following composition:

| Ingredients | Concentration (Percent by Weight) |
|---|---|
| Monoacetin | 5.8 |
| Sorbitan Palmitate | 3.0 |
| Mineral Oil | 56.2 |
| Microcrystalline Wax | 35.0 |

Procedure: To make the oleaginous phase, the mineral oil, microcrystalline wax, and sorbitan palmitate are melted together by heating to 75°-84° C., mixed, and then cooled to about 30°-35° C. The monoacetin is added to the oleaginous phase while mixing. Mixing should be of sufficient intensity to disperse the monoacetin finely and uniformly. The molten product is mixed while cooling to a temperature of 20°-25° C. or lower.

EXAMPLE 5

An ointment base having the following composition:

| Ingredients | Concentration (Percent by Weight) |
|---|---|
| Diacetin | 2.0 |
| Propylene Glycol Stearate | 2.0 |
| Microcrystalline Wax | 35.0 |
| Mineral Oil | 61.0 |

Procedure: To make the oleaginous phase, the microcrystalline wax, mineral oil, and propylene glycol stearate are melted together by heating to 75°-85° C., mixed, and then cooled to about 2°-3° C. above the solidification temperature. The diacetin is added to the oleaginous phase while mixing. Mixing should be of sufficient intensity to disperse the diacetin finely and uniformly. The molten product is mixed while cooling to room temperature.

EXAMPLES 6-7

Ointment bases having the following composition:

| Ingredients | Examples: | |
|---|---|---|
| | 6 | 7 |
| | Concentration (Percent by Weight) | |
| Propylene Glycol | 0.0 | 2.5 |
| Triacetin | 3.5 | 2.5 |
| Mineral Oil | 58.95 | 57.0 |
| Microcrystalline Wax | 35.0 | 35.0 |
| Propylene Glycol Stearate | 2.5 | 3.0 |
| Citric Acid | 0.05 | 0.0 |

Procedure: the mineral oil, microcrystalline wax, and propylene glycol stearate are melted together by heating to 75°-85° C. and mixed, thus making the oleaginous phase. The citric acid, if present, is dissolved in the triacetin by stirring and using heat is necessary. If present, the propylene glycol is added to the traiacetin and mixed. After cooling the oleaginous phase to bout 55° C., the triacetin solution is added to the oleaginous phase while mixing. Mixing should be of sufficient intensity to disperse the triacetin finely and uniformly. Mixing is continued while cooling the ointment to 30° C. or lower. Cooling is accomplished with a cold water bath or heat exchanger.

EXAMPLE 8

An ointment base having the following composition:

| Ingredients | Concentration (Percent by Weight) |
|---|---|
| Triacetin | 10.0 |
| Amerchol CAB* | 30.0 |
| Cholesterol | 1.0 |
| White Petrolatum | 59.0 |

*A proprietary mixture of lanolin alcohol and petrolatum manufactured by Amerchol Corporation Procedure: The Amerchol CAB, white petrolatum, and cholesterol are melted together by heating to 75°-85° C. and mixed to form the oleaginous phase. After cooling the oleaginous phase to about 45° C, the triacetin is added to the oleaginous phase while mixing. Mixing should be of sufficient intensity to disperse the triacetin finely and uniformly. Mixing is continued while cooling the ointment to 30° C. or lower.

EXAMPLE 9

An ointment base having the following composition:

| Ingredients | Concentration (Percent by Weight) |
|---|---|
| Triacetin | 5.0 |
| Dimethicone (1000 centistokes) | 25.0 |
| White Petrolatum | 61.5 |
| Microcrystalline Wax | 5.0 |
| Cholesterol | 1.0 |
| Sucrose Distearate | 2.5 |

Procedure: To make the oleaginous phase, while petrolatum, sucrose distearate, cholesterol, and microcrystalline wax are melted at 75°-85° C. together with the dimethicone and mixed. After cooing the oleaginous phase to about 55° C., the triacetin is added to the oleaginous phase while mixing. Mixing should be of sufficient intensity to disperse the triacetin finely and uniformly.

Mixing is continued while cooling the ointment to 30° C. or lower.

EXAMPLE 10

An ointment base containing an anti-inflammatory corticosteroid medicament having the following composition:

| Ingredients | Concentration (Percent by Weight) |
| --- | --- |
| Betamethasone Dipropionate | 0.064 |
| Propylene Glycol Stearate | 2.5 |
| Triacetin | 3.5 |
| Citric Acid | 0.05 |
| Microcrystalline Wax | 35.0 |
| Mineral Oil | 58.886 |

Procedure: The betamethasone dipropionate and citric acid are dissolved in the triacetin with mixing and heat to 35° C. if needed. The microcrystalline wax, propylene glycol stearate, and mineral oil are melted together by heating to 75°-85° C. while stirring to make the oleaginous phase. After cooling the oleaginous phase to about 55° C., the tiacetin solution is added while mixing to make a homogenous dispersion. Mixing should be of sufficient intensity to disperse the triacetin solution finely and uniformly. Mixing is continued while cooling at room temperature.

EXAMPLE 11

The betamethasone dipropionate ointment in Example 10 was tested in a human basoconstriction bioassay and compared with two other betamethasone dipropionate ointments. The comparison ointments were commercially available products: Diprosone ® (Schering Corp.), a conventional ointment vehicle of mineral oil and white petrolatum; and Diprolene ® (Schering Corp.), an optimized ointment vehicle containing propylene glycol.

For a description of the vasoconstriction bioassay, see Stoughton, R. B., *Archives of Dermatology*, 106: 825-27 (1972); McKenzie, A. W., and R. M. Atkinson, *Archives of Dermatology*, 89: 741-46 (1964); McKenzie, A. W., and R. B. Stoughton, *Archives of Dermatology*, 86: 608-10 (1962); McKenzie, A. W., *Archives of Dermatology*, 86: 611-14 (1962).

About 10 milligrams of each ointment was applied to volar surface of the forearm of volunteers ranging from 18-60 years of age. Test ointments were applied in random order to eight sites, four on each forearm. Each site, into which the ointment samples was rubbed, was about 2 cm in diameter. The sites were protected by a perforated plastic guard that was secured at the ends with tape. The guards remained in place for 16 hours and were then removed. The forearms were immediately washed with soap and water. Two hours later the forearms were inspected by an experienced reader who did not know which ointment has been applied to a particular test site. The readings determined the presence and intensity of vasoconstriction (blanching) at each site.

The scoring was as follows: 0=no vasoconstriction; 1=just discernable basoconstriction; 2=moderate vasoconstriction; 3=marked vasoconstriction. The evaluation was conducted on panels of 15 or 30 human volunteers, and the results were determined by a dermatologist experienced in assessing vasoconstriction. The total score (sum of scores for each test subject) are summarized in Table I. The maximum score possible for 30 subjects is 90. The ointment in Example 10 shows improved vasoconstriction activity compared to the conventional ointment and equal activity to the optimized product. The basoconstriction bioassay has been shown to be a reliable method for predicting clinical efficacy of optical corticosteroid formulations, see Cornell, R. C., and R. B. Stoughton, *Archives of Dermatology*, 121: 63-67 (1985).

TABLE I

| Ointment | Betamethasone dipropionate conc. | Score |
| --- | --- | --- |
| Ex. 10 | 0.064% | 75 |
| Diprosone ® | 0.064% | 56 |
| Diprolene ® | 0.064% | 71 |

EXAMPLE 12

An antiinflammatory corticosteroid ointment having the following composition:

| Ingredients | Concentration (Percent by Weight) |
| --- | --- |
| Fluocinonide | 0.05 |
| Triacetin | 10.0 |
| Citric Acid | 0.05 |
| Amerchol CAB* | 30.0 |
| Cholesterol | 1.0 |
| White Petrolatum | 58.90 |

*A proprietary mixture of lanolin alcohol and petrolatum manufactured by Amerchol Corporation Procedure: The Amerchol CAB, while petrolatum, and cholesterol are melted together by heating to 75°-85° C. and mixed to form the oleaginous phase. The citric acid and fluocinonide are dissolved in the triacetin by stirring and using heat to about 35°-40 C., if necessary. After cooling the oleaginous phase to about 55° C., the triacetin solution is added to the oleaginous phase while mixing with a homogenizing mixer, such as a Silverson or Ross mixer. Mixing should be of sufficient intensity to disperse the triacetin solution finely and uniformly. Mixing is continued while cooling the ointment to 30° C. or lower.

EXAMPLE 13

A vasoconstriction bioassay, as described in Example 11, was conducted on 15 human volunteers in comparison to a commercial fluocinonide ointment, Lidex ® (Syntex Laboratories, Inc.). The fluocinonide ointment of Example 12 performed equally to the commercial ointment that exhibits optimized efficacy. The total vasoconstriction scores from 15 human volunteers are summarized in Table II. The maximum possible score in this experiment was 45.

TABLE II

| Ointment | Fluocinonide conc. | Score |
| --- | --- | --- |
| Ex. 12 | 0.05% | 34 |
| Lidex ® | 0.05% | 33 |

EXAMPLE 14

An antiinflammatory corticosteroid ointment having the following composition:

| Ingredients | (Percent by Weight) |
| --- | --- |
| Fluocinonide | 0.05 |
| Triacetin | 10.00 |
| Citric Acid | 0.05 |
| Propylene Glycol Stearate | 4.00 |
| Microcrystalline Wax | 5.00 |
| White Petrolatum | 80.90 |

Procedure: The microcrystalline wax, white petrolatum, and propylene glycol stearate are melted together by heating to 75°-85° C. and mixed to form the oleaginous phase. The citric acid and fluocinonide are dissolved in the triacetin by stirring and using heat, if necessary. After cooling the oleaginous phase to about 55° C., the triacetin solution is added to the oleaginous phase while mixing. Mixing should be of sufficient intensity to disperse the triacetin solution finely and uniformly. Mixing is continued while cooling the ointment to 30° C. or lower.

What is claimed is:

1. A composition of matter consisting essentially of a glyceryl acetate of the general formula $C_3H_5(CH_3COO)_n(OH)_{3-n}$, wherein n is 1, 2, or 3; an oleaginous material selected from the group consisting of paraffins, silicones, lanolins, and mixtures thereof; a corticosteroid, a surfactant, and a thickener, wherein the glyceryl acetate is a solvent for the corticosteroid and the composition is substantially free from auxiliary solvents.

2. A composition, according to claim 1, wherein the corticosteroid is selected from the group consisting of hydrocortisone, hydrocortisone acetate, hydrocortisone valerate, hydrocortisone butyrate, desonide, triamcinolone acetonide, betamethasone valerate, betamethasone dipropionate, betamethasone benzoate, clobetasol propionate, halcinonide, desoximethasone, amcinonide, fluocinonide, fluandrenolide, alclometasone dipropionate, fluocinolone acetonide, diflorasone diacetate, and mometasone furoate.

3. A composition, according to claim 2, wherein the corticosteroid is selected from the group consisting of betamethasone dipropionate and fluocinonide.

4. A composition, according to claim 1, wherein the concentration of glyceryl acetate is from about 0.25 to about 30 percent by weight.

5. A composition, according to claim 4, wherein the concentration of glyceryl acetate is from about 0.5 to about 12 percent b weight.

6. A composition, according to claim 5, wherein the glyceryl acetate is triacetin (n=3).

7. A composition, according to claim 6, wherein the oleaginous material is selected from the group consisting of paraffins, silicones, lanolins, and mixtures thereof.

8. A composition, according to claim 7 further comprising a surfactant.

9. A composition, according to claim 7, further comprising a thickener.

10. A composition according to claim 7, further comprising an additive selected from the group consisting of buffers, stabilizers, preservatives, colors, and fragrances.

11. A composition of matter consisting essentially of betamethasone dipropionate in a concentration 0.064 percent by weight, triacetin in a concentration 3.5 percent by weight, mineral oil in a concentration 58.886 percent by weight, propylene glycol stearate in a concentration 2.5 percent by weight, microcrystaline wax in a concentration 35 percent by weight, and citric acid in a concentration 0.05 percent by weight, wherein the triacetin is a solvent for the betamethasone and the composition is substantially free from auxiliary solvent.

12. A composition of matter consisting essentially of fluocinonide in a concentration 0.05 percent by weight, triacetin in a concentration 10 percent by weight, white petrolatum in a concentration 80.90 percent by weight, propylene glycol stearate in a concentration 4 percent by weight, microcrystalline wax in a concentration 0.5 percent by weight, and citric acid in a concentration 0.05 percent by weight, wherein the triacetin is a solvent for the fluocinonide and the composition is substantially free from auxiliary solvents.

13. A method of treating a skin disorder comprising applying to the skin a therapeutically effective amount of a corticosteroid incorporated in a vehicle consisting essentially of a glyceryl acetate of the general formula $C_3H_5(CH_3COO)_n(OH)_{3-n}$, wherein n is 1, 2, or 3; an oleaginous material; a surfactant; and a thickener; wherein the glyceryl acetate is a solvent for the corticosteroid and the composition is substantially free from auxiliary solvents.

14. A method, according to claim 13, wherein the corticosteroid is selected from the group consisting of hydrocortisone, hydrocortisone butyrate, desonide, triamcinolone acetonide, betamethasone valerate, betamethasone dipropionate, betamethasone benzoate, clobetasol propionate, halcinonide, desoximethasone, amcinonide, fluocinonide, fluandrenolide, alclometasone dipropionate, fluocinolone acetonide, diflorasone diacetate, and mometasone furoate.

15. A method, according to claim 14 wherein the corticosteroid is selected from the group consisting of betamethasone dipropionate and fluocinonide.

16. A method of treating a skin disorder comprising applying to the skin a composition of matter consisting essentially of betamethasone dipropionate in a concentration 0.064 percent by weight, triacetin in a concentration 3.5 percent by weight, mineral oil in a concentration 58.886 percent by weight, propylene glycol stearate in a concentration 2.5 percent by weight, microcrystalline wax in a concentration 35 percent by weight, and citric acid in a concentration 0.05 percent by weight, wherein the triacetin is a solvent for the betamethasone and the composition is substantially free from auxiliary solvent.

17. A method of treating skin disorders comprising applying to the skin a composition of matter consisting essentially of fluocinonide in a concentration 0.05 percent by weight, triacetin in a concentration 10 percent by weight, white petrolatum in a concentration 80.90 percent by weight, propylene glycol stearate in a concentration 4 percent by weight, microcrystalline wax in a concentration 5 percent by weight, and citric acid in a concentration 0.05 percent by weight, wherein the triacetin is a solvent for the fluocinonide and the composition is substantially free from auxiliary solvents.

* * * * *